United States Patent [19]

Woo et al.

[11] Patent Number: 4,713,442
[45] Date of Patent: Dec. 15, 1987

[54] POLYAROMATIC CYANATE

[75] Inventors: Edmund P. Woo, Midland; Daniel J. Murray, Saginaw, both of Mich.

[73] Assignee: The Dow Chemical Company, Midland, Mich.

[21] Appl. No.: 833,931

[22] Filed: Feb. 27, 1986

Related U.S. Application Data

[62] Division of Ser. No. 522,234, Nov. 16, 1985, Pat. No. 4,631,700.

[51] Int. Cl.⁴ .............................................. C08G 73/00
[52] U.S. Cl. ...................................... 528/422; 544/193
[58] Field of Search .......................... 528/422; 544/193

[56] References Cited

U.S. PATENT DOCUMENTS

| | | | |
|---|---|---|---|
| 3,107,261 | 10/1963 | Gerber et al. | 260/453 |
| 3,285,730 | 11/1966 | Weis et al. | 71/2.3 |
| 3,308,101 | 3/1967 | Ikeda | 528/422 |
| 3,383,359 | 5/1968 | Weitzel et al. | 260/47 |
| 3,448,079 | 6/1969 | Grigat et al. | 260/59 |
| 3,502,617 | 3/1970 | Schminke et al. | 260/47 |
| 3,553,244 | 1/1971 | Grigat et al. | 260/453 |
| 3,562,214 | 2/1971 | Kubens et al. | 260/47 |
| 3,595,900 | 7/1971 | Burkhardt et al. | 260/453 |
| 3,658,623 | 4/1972 | Grigat et al. | 156/331 |
| 3,694,410 | 9/1972 | Oehmke | 260/47 R |
| 3,738,962 | 6/1973 | Loudas et al. | 260/47 R |
| 3,740,348 | 6/1973 | Grigat et al. | 260/453 AL |
| 3,755,402 | 8/1973 | Grigat et al. | 260/453 AR |
| 3,817,920 | 6/1974 | Langager | 260/47 R |
| 3,978,028 | 8/1976 | Sundermann et al. | 260/61 |
| 3,994,949 | 11/1976 | Meyer et al. | 260/453 P |
| 4,028,393 | 6/1977 | Rottloff et al. | 260/453 P |
| 4,031,067 | 6/1977 | Sundermann et al. | 260/77.5 R |
| 4,046,796 | 9/1977 | Rottloff et al. | 260/453 P |
| 4,049,630 | 9/1977 | Sundermann et al. | 260/47 R |
| 4,059,567 | 11/1977 | Sundermann et al. | 260/47 R |
| 4,094,852 | 6/1978 | Sundermann et al. | 260/37 N |
| 4,097,455 | 6/1978 | Burkhardt et al. | 260/47 CB |
| 4,110,364 | 8/1978 | Gaku et al. | 528/170 |
| 4,195,132 | 3/1980 | Sundermann et al. | 521/155 |
| 4,371,689 | 2/1983 | Gaku et al. | 528/162 |
| 4,390,680 | 6/1983 | Nelson | 528/97 |
| 4,394,497 | 7/1983 | Nelson et al. | 528/101 |
| 4,528,366 | 7/1985 | Woo et al. | 528/422 |

FOREIGN PATENT DOCUMENTS 1183507 of 1965 Fed. Rep. of Germany .
1190184 4/1965 Fed. Rep. of Germany .
1526035 9/1978 United Kingdom .

OTHER PUBLICATIONS

Chemical Abstract 87(8):54042e, (Sundermann et al.)

Primary Examiner—Harold D. Anderson

[57] ABSTRACT

This invention relates to a polyaromatic cyanate which corresponds to the formula

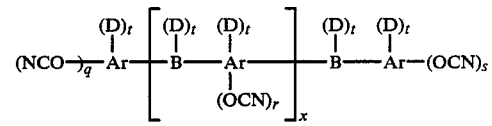

wherein:
  Ar is an aromatic radical;
  B is a $C_{7-20}$ polycyclic aliphatic radical;
  D is independently in each occurrence any nonactive hydrogen-containing substituent;
  q, r and s are independently in each occurrence the integers 0, 1, 2, or 3; with the proviso that the sum of q, 4 and s is greater than or equal to 2;
  t is independently in each occurrence an integer of between about 0 and 4 inclusive; and
  x is a number between about 0 and 5 inclusive.

Another aspect of this invention is a novel polytriazine which comprises the reaction product of the polyaromatic cyanate esters of this invention. The novel polytriazines may further comprise the reaction product of the novel polyaromatic cyanates of this invention in admixture with other cyanates known in the art as useful for the preparation of polytriazines.

10 Claims, No Drawings

POLYAROMATIC CYANATE

CROSS-REFERENCE TO RELATED APPLICATION

This is a divisional of application Ser. No. 552,234, filed Nov. 16, 1985, U.S. Pat. No. 4,631,700, 12-23-86.

BACKGROUND OF THE INVENTION

The invention relates to novel polyaromatic cyanates, a novel process for preparing the polyaromatic cyanates and to novel polytriazines prepared from the polyaromatic cyanates.

It is known from German Patent Specification No. 1,190,184 that high molecular weight polytriazines can be obtained by polymerizing difunctional or polyfunctional aromatic cyanates at elevated temperature, optionally in the presence of polymerization promoters. The polymers are characterized for example by their remarkable stability at elevated temperatures and they are duroplastic in character after tempering for a sufficiently long period. The resistance of the polytriazines to acids and various solvents may also be emphasized.

In addition, it was found by V. V. Korchak et al. (cf. Vysokomolekulyarnye Soedineniya 1974, number 1, pages 15 to 21) that the thermal and thermo-oxidative destruction of polytriazines based on aromatic cyanates is greatly influenced by moisture.

Finally, it is known from German Pat. No. 1,720,740 that polyfunctional aromatic cyanates can be combined with powder-form and/or fibrous fillers or reinforcing materials and subjected either to a preliminary or subsequent heat treatment at about 50° C. to 150° C., the resulting molding composition molded and hardened at temperatures in the range from about 150° C. to 250° C. In many cases the resulting moldings also show inadequate thermal stability after storage in a moist, tropical atmosphere.

Polyaromatic cyanates which prepare polytriazines which are hydrolytically stable are needed. Polyaromatic cyanates which are useful in preparing polyaromatic triazines which are thermally stable are further needed.

SUMMARY OF THE INVENTION

The invention involves a polyaromatic cyanate which corresponds to the formula

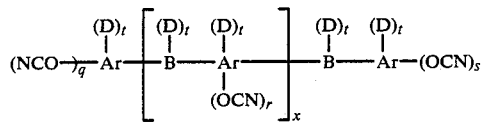

wherein:
Ar is an aromatic radical;
B is a $C_{7-20}$ polycyclic aliphatic radical;
D is any nonactive hydrogen-containing substituent;
q, r and s are independently in each occurrence the integers 0, 1, 2, or 3; with the proviso that the sum of q, r and s is greater than or equal to 2;
t is independently in each occurrence an integer of between about 0 and 4; and
x is a number between about 0 and 5.

Another aspect of this invention is a method for the preparation of the polyaromatic cyanates. This process generally comprises first preparing a cyanogen chloride in situ by contacting a solution of chlorine in a chlorinated hydrocarbon with an aqueous solution of alkali metal cyanide. Then the aqueous layer containing the alkali metal chloride by-product is separated from the chlorinated hydrocarbon layer containing the cyanogen chloride. Then a solution of a polycyclic bridged hydroxy-substituted polyaromatic phenol in a suitable solvent is contacted with the cyanogen chloride solution in the presence of a teritiary amine to prepare the polyaromatic cyanates of this invention.

Another aspect of this invention is a novel polytriazine which comprises the reaction product of the polyaromatic cyanate esters of this invention. The novel polytriazines may further comprise the reaction product of the novel polyaromatic cyanates of this invention in admixture with other cyanates known in the art as useful for the preparation of polytriazines.

The novel polyaromatic cyanates of this invention prepare polytriazines which are surprisingly more stable to hydrolysis than prior art polytriazines.

The polytriazines of this invention can be used as cure-in-place resins or fabricated in the form of shaped articles, where thermal stability, chemical inertness and solvent resistance are desirable or required.

DETAILED DESCRIPTION OF THE INVENTION

Aromatic radical, Ar, refers herein any radical containing an aromatic group. Examples of aromatic radicals include benzene, naphthalene, phenanthracene, anthracene, or biaromatic radicals, or two or more aromatic radicals bridged by alkylene moieties. Ar is preferably a benzene, naphthalene, biphenyl, benaphthyl, or a diphenylalkylene radical. Ar is more preferably a benzene radical.

Polycyclic aliphatic radical refers herein to any aliphatic radical which contains two or more cyclic rings. The polycyclic aliphatic radicals may contain one or more double or triple bonds. Preferred polycyclic aliphatic radicals correspond to the formulas

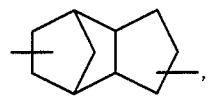 II

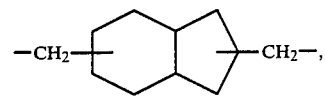 III

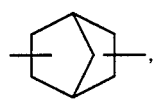 IV

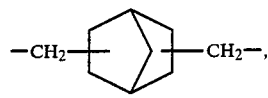 V

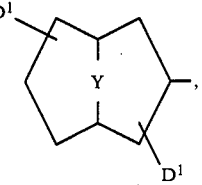 VI

-continued

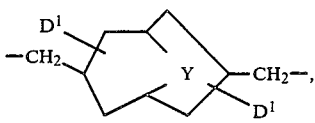

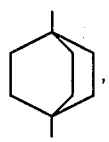

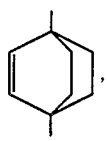

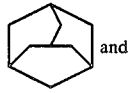

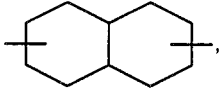

wherein:
Y is CH$_2$, S,

and
D$^1$ is C$_{1-5}$ alkyl.

B is more preferably a radical which corresponds to one of the formulas II, III, IV, V, VI, VII, VIII or XIII with radicals corresponding to formulas II, III, IV, V or XIII being even more preferred, and radicals corresponding to formula II being most preferred.

D is any substituent which can be substituted on an organic hydrocarbon radical, with the exception that the substituent cannot contain an active hydrogen atom.

Substituents within the scope of this invention are well-known to those skilled in the art. Active hydrogen atom means herein a hydrogen atom which is bonded to an oxygen, sulfur or nitrogen atom. Examples of substituents within the scope of D include alkyl, alkenyl, alkynyl, aryl, alkaryl aralkyl, halo, alkoxy, nitro, carboxylate, sulfone, sulfide or carbonate moieties. Preferred substituents are C$_{1-10}$ alkyl, C$_{1-10}$ alkenyl, nitro, and halo moieties, with C$_{1-3}$ alkyl, C$_{1-3}$ alkynyl, bromo and chloro moieties being most preferred.

Preferably, q, r and s are independently 1 or 2, and are most preferably 1. Preferably, t is independently an integer of 0, 1 or 2, more preferably 0 or 1, and most preferably 0. Preferably, x is between about 0 and 2 inclusive, and more preferably between about 0 and 1 inclusive.

The polyaromatic cyanates of this invention usually exist as a mixture of many isomers. Further, these polyaromatic cyanates usually are found as a mixture of compounds in which x is between 0 and 5. Usually the number given for x in a particular mixture is an average number.

In one preferred embodiment the polyaromatic cyanates correspond to the formula

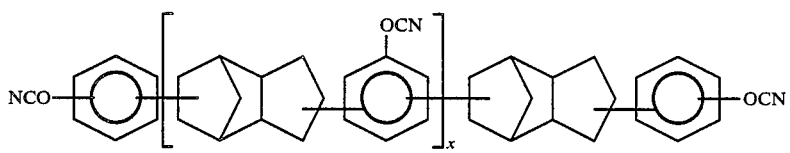

wherein x is a real number of between about 0 and 5, inclusive.

The polyaromatic cyanate esters of this invention are generally prepared by contacting a suitable polyaromatic phenol with cyanogen chloride, in the presence of a teritiary amine. It is preferable to prepare the cyanogen chloride in situ by contacting a solution of chlorine in a chlorinated hydrocarbon solvent with an aqueous solution of alkali metal cyanide. The reaction mixture separates into an organic layer of the chlorinated hydrocarbon containing cyanogen chloride and an aqueous layer containing the alkali metal chloride salt. Generally, the alkali metal cyanide and chlorine are reacted in a molar ratio of between 1.0:1.0 and 1.0:1.15, preferably between about 1.0:1.0 and 1.0:1.05; and most preferably about 1.0:1.0. An excess of either may result in undesirable consequences, that is, excess chlorine may later react with the phenol, and excess alkali metal cyanide may result in a lower product purity. This contacting is done at a temperature of 0° C. or below, preferable less than −15° C. Above 0° C. the cyanogen chloride will trimerize. Preferable solvents for the chlorine are the aliphatic chlorinated hydrocarbons, such as methyl chloride, chloroform, 1,1,1-trichloroethane and the like. The preferred alkali metal cyanide is sodium cyanide.

The aqueous layer and organic layer are then separated. The separation of the organic layer from the aqueous layer is advantageous as the presence of the aqueous layer in further processing adversely affects the purity of the polyaromatic cyanates eventually prepared.

The organic layer containing the cyanogen chloride is then contacted with polycyclic bridged hydroxy-substituted polyaromatic compound dissolved in a suitable solvent in the presence of a tertiary amine.

Polycyclic bridged hydroxy-substituted polyaromatic compounds useful in this process correspond to the formula

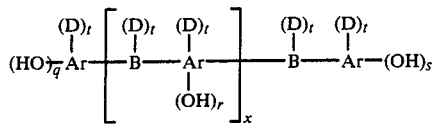

wherein Ar, B, D, q, r, s, t and x are as defined hereinbefore.

In one preferred embodiment the polycyclic bridged hydroxy-substituted polyaromatic compounds correspond to the formula

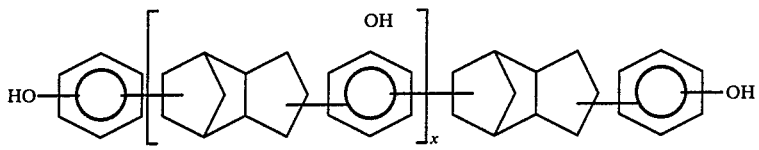

wherein x is as defined hereinbefore. The polycyclic bridged hydroxy-substituted polyaromatic compounds used usually exist as a mixture of isomers. Further, the polycyclic bridged hydroxy-substituted polyaromatic compounds are found as a mixture of compounds in which x is between 0 and 5. Usually the number given for x is an average number. The solvents used for the polycyclic bridged hydroxy-substituted polyaromatic compounds are secondary alcohols, tertiary alcohols, or chlorinated hydrocarbons. Preferred solvents are secondary alcohols or aliphatic chlorinated hydrocarbons, with isopropyl alcohol and methylene chloride most preferred.

The process is preferably done at a temperature of 0° C. or below, more preferably $-15°$ C. or below.

For complete conversion of the hydroxy moieties on the aromatic radicals to cyanate moieties, at least 1 mole of cyanogen chloride for each hydroxy equivalent is needed. It is preferable to use an excess of 10 mole percent of cyanogen chloride for each hydroxy equivalent to insure complete conversion.

The tertiary amine acts as a hydrochloride acceptor, and as a result a tertiary amine hydrochloride salt is a by-product of the process. Generally, at least one mole of tertiary amine for each hydroxy equivalent is used. Hydroxy equivalent refers herein to the average molecular weight of the polycyclic bridged hydroxy-substituted polyaromatic compound divided by the average number of hydroxy moieties per molecule.

The polyaromatic cyanates can be recovered from the reaction solution in the following manner. The reaction mixture is first contacted with a dilute aqueous solution of base, such as a bicarbonate, to remove the excess cyanogen chloride. Then the reaction mixture is contacted with water to remove the tertiary amine hydrogen chloride salt. Thereafter, the reaction solution is contacted with a dilute aqueous acid solution to neutralize any base present. A 1–20 weight percent solution of hydrochloride, phosphoric or sulfuric acid can be used, preferably a 5–10 weight percent solution. The reaction solution is then contacted with water to remove any impurities which may be present. The reaction solution is dried over a dessicant to remove the water, and the solvent is stripped off.

The polyaromatic cyanate recovered is of surprisingly high purity and can be used directly to prepare polytriazines.

The polycyclic bridged hydroxy-substituted polyaromatic compounds useful in this invention can be prepared by reacting an aromatic compound, containing at least one aromatic hydroxy moiety and one position on the aromatic ring which can be alkylated, with an unsaturated polycyclic aliphatic compound under conditions such that a polycyclic bridged hydroxy-substituted polyaromatic compound useful in this invention is prepared.

Suitable substituted aromatic hydroxy compounds which can be employed herein include any such compounds which contain one or two aromatic rings, at least one phenolic hydroxyl group and at least one ortho or para ring position with respect to a hydroxyl group available for alkylation.

Particularly suitable hydroxy-substituted aromatic compounds which can be employed herein include, for example, phenol, chlorophenol, bromophenol, methylphenol, hydroquinone, catechol, resorcinol, guaiacol, pyrogallol, phloroglucinol, isopropylphenol, ethylphenol, propylphenyl, t-butylphenol, isobutylphenol, octylphenol, nonylphenol, cumylphenol, p-phenylphenol, o-phenylphenol, m-phenylphenol, bisphenol A, dihydroxydiphenyl sulfone, mixtures thereof and the like.

The hydroxy-substituted polyaromatic compound is contacted with the unsaturated polycyclic aliphatic compound optionally in the presence of a solvent. Preferred solvents include chlorinated hydrocarbons, aliphatic hydrocarbons, aromatic hydrocarbons and nitro-substituted hydrocarbons. In general the hydroxy-substituted polyaromatic compound is contacted with the unsaturated polycyclic aliphatic compound in a mole ratio of between about 20.0:1.0 and 1.0:1.0, preferably between about 10.0:1.0 and 1.5:1.0.

These reactants are preferably contacted in the presence of a catalyst.

Acid catalysts which can be employed herein include, for example, Lewis acids, alkyl, aryl and aralkyl sulfonic acids, and disulfonic acids of diphenyloxide and alkylated diphenyloxide, sulfuric acid, mixtures thereof and the like. Preferable catalysts are such Lewis acids as $BF_3$ gas, organic complexes of boron trifluoride such as those complexes formed with phenol, cresol, ethanol, acetic acid and the like. Also Lewis acids include aluminum chloride, zinc chloride, stannic chloride, and the like. Also catalysts include, for example, activated clays, silica, silica-alumina complexes, and the like.

In preparing the compounds which contain an average of more than one phenolic hydroxyl group and more than one aromatic ring per molecule, the reaction between the phenolic hydroxyl-containing compounds and the unsaturated hydrocarbons can be conducted at temperatures of from about 33° C. to about 270° C., preferably from about 33° C. to about 210° C.

The polyaromatic cyanates of this invention are useful in preparing polytriazines. The polytriazines of this invention comprise the reaction product of (a) between about 1 and 100 percent by weight of the polyaromatic cyanate of this invention, and (b) between about 0 and 99 percent by weight of a cyanate which is useful for preparing triazines, such cyanates being well-known to those skilled in the art. The prior art cyanates useful in this invention includes those corresponding to the formula Ar—(OCN)$_n$ wherein Ar is an aromatic radical, and n is an integer of from 1 to 5. Preferable cyanates include those corresponding to the formula

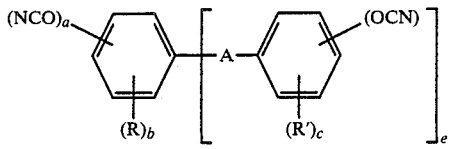

wherein
each R is the same or different and represents hydrogen, halogen, straight and branched $C_1$–$C_{20}$ alkyl, phenyl, alkoxy radicals having from 1 to 4 carbon atoms, alkoxy carbonyl radicals having from 1 to 4 carbon atoms in the alkyl group; or two adjacent radicals R on the same nucleus may together form a carbocyclic 5- or 6-membered ring, two adjacent radicals R may, together with a hetero atom (O, S, N), form a 5- or 6-membered heterocyclic ring,
R' has the same meaning as R or represents the group

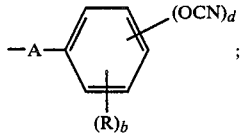

A represents a direct bond, a $C_1$–$C_{20}$ alkylene group optionally substituted by $C_1$–$C_4$ alkyl or phenyl, a cycloaliphatic or aromatic 5- or 6-membered ring optionally interrupted by oxygen, a sulfonyl group (—SO$_2$—), a carbonyl dioxide group,

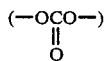

or a carbonyl group;
a represents a number of from 1 to 5 when e≧1, and a number of from 2 to 5 when e=0;
b represents 5−a when e≦1 and 6−(a+d) when e=0;
c represents 5−d;
d represents a number of from 0 to 5, and
e represents 0, 1, 2 or 3,
with a provision that the sum of a and d is always a number from 2 to 5.

The following compounds are specifically mentioned as examples of conventional cyanates within one or more of the formulas noted above: 1,3- and 1,4-dicyanatobenzene, 2-tert-butyl-1,4-dicyanatobenzene, 2,4-dimethyl-1,3-dicyanatobenzene, 2,5-di-tert-butyl-1,4-dicyanatobenzene, tetramethyl-1,4-dicyanatobenzene, 2,4,6-trimethyl-1,3-dicyanatobenzene, 4-chloro-1,3-dicyanatobenzene, 1,3-, 1,4-, 1,5-, 1,6-, 1,7-, 1,8-, 2,6- or 2,7-dicyanatonaphthalene, 1,3,5-tricyanatobenzene; 4,4'-dicyanatodiphenyl, 2,2'-dicyanatodiphenyl, 3,3',5,5'-tetramethyl-4,4'-dicyanatodiphenyl, 3,3',5,5'-tetrachloro-4,4'-dicyanatodiphenyl, 3,3',5,5'-tetrachloro-2,2'-dicyanatodiphenyl, 2,2',6,6'-tetrachloro-4,4'-dicyanatodiphenyl, 4,4'-bis-[(3-cyanato)-phenoxy]-diphenyl, 4,4'-bis-[(4-cyanato)-phenoxy]-diphenyl; 2,2'-dicyanato-1,1'-binaphthyl; 4,4'-dicyanatodiphenyl ether, 3,3',5,5'-tetramethyl-4,4'-dicyanatodiphenyl ether, 3,3',5,5'-tetrachloro-4,4'-dicyanatodiphenyl ether, 4,4'-bis-[p-cyanatophenoxy]-diphenyl ether, 4,4'-bis-[p-cyanatophenylisopropyl]-diphenyl ether, 4,4'-bis-[p-cyanatophenoxy]-benzene, 4,4'-bis-[m-cyanatophenoxy]-diphenyl ether, 4,4'-bis-[4-(4-cyanatophenoxy)-phenyl sulfone]-diphenyl ether; 4,4'-dicyanatodiphenyl sulfone, 3,3',5,5'-tetramethyl-4,4'-dicyanatodiphenyl sulfone, 3,3',5,5'-tetrachloro-4,4'-dicyanatodiphenyl sulfone, 4,4'-bis-[p-cyanatophenylisopropyl]-diphenyl sulfone, 4,4'-bis-[(4-cyanato)-phenoxy]-diphenyl sulfone, 4,4'-bis-[(3-cyanato)-phenoxy]-diphenyl sulfone, 4,4'-bis-[4-(4-cyanatophenylisopropyl)-phenoxy]-diphenyl sulfone, 4,4'-bis-[4-cyanatophenyl sulfone)-phenoxy]-diphenyl sulfone, 4,4'-bis-[4-(4-cyanato)-diphenoxy]-diphenyl sulfone, 4,4'-dicyanatodiphenyl methane, 4,4'-bis-[p-cyanatophenyl]-diphenyl methane, 2,2-bis-(p-cyanatophenyl)-propane, 2,2-bis-(3,5-dimethyl-4-cyanatophenyl)-propane, 2,2-bis-(3,5-dichloro-4-cyanatophenyl)-propane, 1,1-bis-[p-cyanatophenyl]-cyclohexane, bis-[2-cyanato-1-naphthyl]-methane, 1,2-bis-[p-cyanatopheyl]-1,1,2,2-tetramethyl ethane, 4,4'-dicyanatobenzophenone, 4,4'-bis-(4-cyanato)-phenoxybenzophenone, 1,4-bis-[p-cyanatophenylisopropyl]-benzene, 2,2',5,5'-tetracyanatodiphenyl sulfone; polycyanic acid esters of novolaks (reaction products of phenol or alkyl- or halogen-substituted phenols with formaldehyde in acid solution) having from 3 to 5 OCN groups and the like. Preferred conventional cyanate containing compounds include 2,2-bis(p-cyanatophenyl)-propane and 2,3-bis-(3,5-dibromo-4-cyanatophenyl)-propane.

The polytriazines of this invention preferably comprise the reaction product of (a) between about 25 and 100 percent by weight of the polyaromatic cyanates of this invention, and (b) between 0 and 75 percent by weight of a cyanate which is useful in preparing polytriazines. More preferably, the polytriazines of this invention comprise the reaction product (a) between about 50 and 100 percent by weight of a polyaromatic cyanate of this invention, and (b) between about 0 and 50 percent by weight of a cyanate useful in preparing polytriazines. The prior art cyanates may comprise mono-, di- and polycyanates.

The polytriazines of this invention may comprise up to 30 percent of monocyanate compounds, for example, Ar—(OCN)$_n$ wherein n=1. The use of monocyanates give the polytriazines modified properties, for example, solubility, glass transition temperature, moisture resistance and impact resistance.

The formation of polytriazines arise from the cyclotrimerization of aryl cyanates to prepare 1,3,5-triaryloxytriazines. The use of the difunctional and polyfunctional polyaromatic cyanates of this invention in the cyclotrimerization process results in the preparation of a three dimensional network polymer which is hard, infusible and insoluble.

The term polytriazines as used in this invention refer to both fully cured polytriazines polymers, and partially cured polytriazine prepolymers. Fully cured polytriazines are essentially free of cyanate functionalities. The prepolymers are cyanate group-containing polytriazines of liquid, wax-like or solid consistency and are soluble in organic solvents. These prepolymers are highly stable in storage. These prepolymers may be later converted to high molecular weight polytriazines when exposed to polymerization conditions. Prepolymers are prepared to permit easy handling of a resin prior to final use. Further, these prepolymers are useful in the production of coatings on such substrates as metals, cermics, glass and earthenware, and as impregnating lacquers or laminating resins.

In the preparation of the polytriazines, aromatic polycyanates are contacted in the presence of a catalyst at a temperature of between about 20° C. and 200° C., optionally in the presence of a solvent. Preferable temperatures are between about 80° C. and 180° C. The prepolymers are prepared by the same process, except either a lower temperature or a lower amount of catalyst is used, so that the aromatic polycyanates do not completely polymerize.

The rate of polymerization is dependent upon the temperature and the catalyst amount. As either, or both, increase, the rate of polymerization increases. At higher temperatures, a lower amount of catalyst is necessary for the desired amount of polymerization than is necessary at lower temperatures.

Useful catalysts include acids, bases, salts, nitrogen and phosphorus compounds, for example, Lewis acids such as $AlCl_3$, $BF_3$, $FeCl_3$, $TiCl_4$, $ZnCl_2$, $SnCl_4$; proton acids such as HCl, $H_3PO_4$; aromatic hydroxy compounds such as phenol, p-nitrophenol, pyrocatechol, dihydroxy naphthalene, sodium hydroxide, sodium methylate, sodium phenolate, trimethylamine, triethylamine, tributylamine, diazobicyclo-(2,2,2)-octane, quinoline, isoquinoline, tetrahydroisoquinoline, tetraethyl ammonium chloride, pyridine-N-oxide, tributylphosphine, phospholine-$\Delta^3$-1-oxa-1-phenyl, zinc octoate, tin octoate, zinc naphthenate, cobalt salts of $C_{6-20}$ carboxylic acids and mixtures thereof. Preferable catalysts are the cobalt salts of $C_{6-20}$ carboxylic acids, with cobalt naphthenate and cobalt octoate being most preferred.

Generally, any amount of catalyst which catalyzes the preparation of polytriazines is suitable. Preferably, between about 0.001 and 10 percent by weight of the cyanates of catalyst is used.

Solvents useful in this invention can be any compound which dissolves the aromatic polycyanates and does not interfere with the reaction. Suitable solvents include aromatic hydrocarbons, alcohols and ketones.

The polyfunctional aromatic polycyanates may be combined with the powder-form or fibrous fillers or reinforcing materials either before or after heat treatment of the aromatic polycyanates and by basically any method. For example it is possible to impregnate powder-form or fibrous fillers or reinforcing materials such as quartz sand or glass cloths, with the aromatic cyanates, optionally in solution. Examples of the solvents which may be used for this purpose and which, generally, have to be removed again afterwards, are inert solvents such as methylene chloride, acetone, methylethyl ketone, xylene, ethyl acetate benzene, toluene, tetrahydrofuran, chlorobenzene, dibutyl ether, dimethyl formamide and tetramethylene sulfone.

Suitable fillers and reinforcing materials are, generally, in any powder form and/or fibrous products, for example, of the type commonly used in the production of moldings based on unsaturated polyester resins or epoxide resins. Examples of products such as these are, primarily, granular fillers such as quartz powder, ground shale, asbestos powder, powdered corundum, chalk, iron powder, aluminum powder, sand, gravel and other fillers of this kind, also inorganic or organic fibers, more especially glass fibers in the usual textile forms of fibers, filaments, rovings, yarns, nonwovens, mats and cloths, etc. In this connection, amino silane-based finishes have proven to be particularly effective. It is also possible to use corresponding textile structures of organic, preferably synthetic fibers (polyamides, polyesters) or on the basis of quartz, carbon, metals, etc., as well as monocrystals (whiskers).

The end products combined with fillers or reinforcing materials may be used in particular in vessel and pipe construction by the winding technique, in electrical engineering, in mold construction and tool making and also in the construction of heavily stressed components, in the lightweight construction of vehicles in aeronautical and astronautical engineering.

SPECIFIC EMBODIMENTS

The following examples are included for illustrative purposes only, and are not intended to limit the scope of the invention or claims.

EXAMPLE 1

Polytriazine castings of each of the following cyanate-containing compounds are prepared.

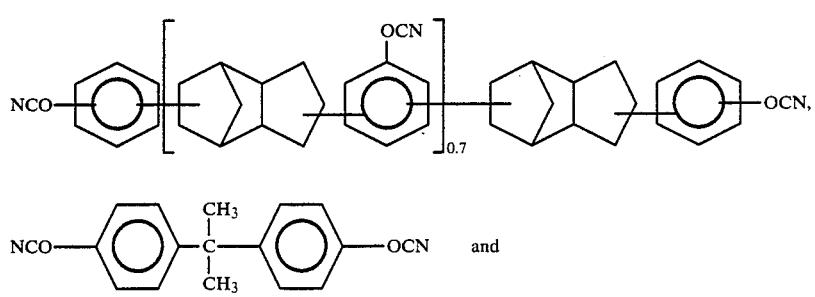

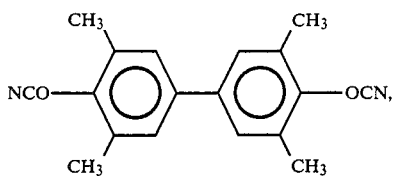

wherein formula I is an example of this invention and formulas II and III are not.

The polytriazine castings of the aromatic cyanates of formulas I and II are prepared by heating about 6 g of the respective cyanate along with about 200 parts per million of cobalt naphthenate at 150° C. for 1 hour and 20 minutes and then at 200° C. for 3 hours.

The castings of formula III are prepared by heating about 6 g of formula III along with about 200 parts per million of cobalt naphthenate at 180° C. for 2 hours and 250° C. for 90 minutes.

All of the castings are monitored by differential scanning calorimetry to insure the castings have no uncured cyanate functionalities.

A casting of each of the polytriazines is exposed to the following test conditions. In Test 1, the castings are boiled in water for 96 hours. In Test 2, the castings are immersed in 20 weight percent hydrochloric acid for 2.5 hours at room temperature and then at reflux for 4.5 hours. In Test 3, the castings are immersed in 40 weight percent sodium hydroxide at room temperature for 2.5 hours, then at reflux for 4.5 hours.

Each casting is weighed before and after each test. Table I compiles the test results.

TABLE I

| Test | Weight Change (%) | | |
|---|---|---|---|
| | Cyanate I | Cyanate II | Cyanate III |
| 1 | +0.63 | +1.08 | +1.26 |
| 2 | +0.26 | −4.35 | +1.55 |
| 3 | −1.69 | −28.68 | −5.78 |

The weight gains are due to the adsorption of water by the samples. The weight losses are due to the decomposition of the polymer due to hydrolysis. Generally, water is adsorbed by the polymer prior to hydrolysis.

The example demonstrates that the polytriazine prepared from the compound corresponding to formula I is significantly more resistant to hydrolysis than the polytriazines prepared from compounds corresponding to formula II or III. Visual inspection of the castings after Test 2 shows that the casting prepared from the compound corresponding to formula I has no change in appearance, whereas the casting prepared from the compound corresponding to formula II has lost its transparency due to surface pitting. A visual inspection after Test 3 of the casting prepared from the compound corresponding to formula I shows slight surface pitting, whereas a visual inspection of the castings prepared from the compound corresponding to formula II after Test 3 shows the casting to have numerous voids throughout and that the casting readily crumbles under physical stress.

EXAMPLE 2

An 85 percent solution of polyaromatic cyanate I in methyl isobutyl ketone containing 0.016 weight percent of cobalt naphthenate are used to impregnate fiberglass cloth. Eight plys of the impregnated cloth are laid up and cured in a press at 175° C. and 300 psi for 1 hour to give a 0.062 inch thick laminate which has a glass transition temperature of 265° C. The laminate shows a 0.09 percent by weight absorption of water after boiling for an hour at 15 psi.

EXAMPLE 3

A 50 percent solution of a polyaromatic cyanate corresponding to the formula

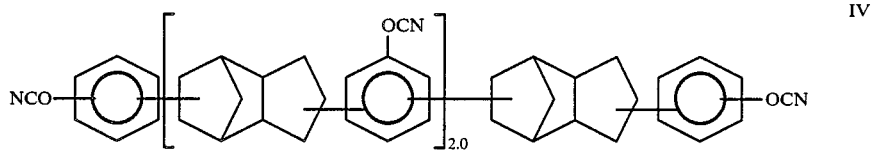

in methyl ethyl ketone containing 0.02 percent of cobalt octoate is used to impregnate fiberglass cloth, six plys of which are laid up and cured in a press at 175° C. and 300 psi for 1 hour. A laminate using the polyaromatic cyanate of formula II (not an example of the invention) is prepared in the same manner. Both laminates are subjected to humidity aging at 71° C. for 1000 hours at 100 percent humidity. The laminate prepared from formula IV shows water absorption of 0.59 percent, while the laminate prepared from formula II absorbs 0.83 percent water (the experimental error is 0.01 percent). This example demonstrates that the polytriazines prepared from polyaromatic cyanates of this invention absorb significantly less water than polytriazines prepared from prior art cyanates.

EXAMPLE 4

A fiberglass cloth laminate is prepared from a 50 percent solution of formula IV in methyl ethyl ketone without catalyst. The laminate is heated at 150° C. for 15 minutes, and then inserted into a 215° C. press at contact pressure. The temperature is raised to 250° C. over a period of 8 minutes and a pressure of 100 psi is then applied. After 45 minutes, the laminate is removed and post-cured for 1 hour at 250° C. and then for 1 hour at 275° C. The laminates are of an E glass Style 7781, A 1100 Finish, 6-ply and 27 percent resin.

The laminate is divided into different portions and several tests are run. In the control, the flexural strength and flexural modulus are determined at room temperatures (23° C.) and 190° C. This testing is done in accordance with ASTM D-790 (incorporated herein by reference). Other portions of the laminate are exposed to different conditions and thereafter the flexural strength and flexural modulus are tested.

In Test 4 the laminate is exposed to air at 200° C. for 500 hours. In Test 5 the laminate is exposed to 100 percent humidity at 50° C. for 570 hours. In Test 6 the laminate is immersed in CH₂Cl₂ for 7 days. In Test 7 the laminate is immersed in methanol for 7 days. In Test 8 the laminate is immersed in toluene for 7 days. The percentage of the flexural strength and modulus of each laminate compared to the control at room temperature is calculated. The laminates are also weighed before and after each treatment and the percent change relative to the standard is calculated. The results are compiled in Table II.

Table II demonstrates that glass laminates prepared using the polyaromatic cyanates of this invention are stable to heat, humidity and contact with common solvents such as methanol and toluene.

TABLE II

| | | Flexural Strength | | | | Flexural Modulus | | | |
|---|---|---|---|---|---|---|---|---|---|
| | | room temperature | | 190° C. | | room temperature | | 190° C. | |
| Test | Weight Change | 10³ psi | % of Standard | 10³ psi | % of Standard | 10³ psi | % of Standard | 10³ psi | % of Standard |
| Standard | — | 70.5 | — | 66.0 | 94 | 3.08 | — | 3.19 | 103 |
| 4 | −0.23 | 63.7 | 90 | 58.9 | 84 | 3.23 | 105 | 3.12 | 101 |
| 5 | +0.4 | 72.5 | 103 | 56.6 | 80 | 3.49 | 113 | 2.79 | 91 |
| 6 | +12.56 | 43.5 | 62 | — | — | 2.09 | 68 | — | — |
| 7 | +0.69 | 57.1 | 80 | — | — | 3.24 | 105 | — | — |
| 8 | +0.27 | 73.3 | 104 | — | — | 3.21 | 104 | — | — |

What is claimed is:

1. A polytriazine which comprises 1,3,5-triaryloxy-triazines which comprise the reaction product of
(a) between about 1 and 100 mole percent of an aromatic polycyanate which corresponds to the formula

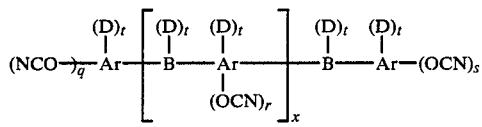

wherein
Ar is an aromatic radical;
B is a C₇₋₂₀ polycyclic aliphatic radical;
D is independently in each occurrence any nonactive hydrogen-containing substituent;
q, r, and s are independently in each occurrence the integers 0, 1, 2, or 3;
with the proviso that the sum of q, r, and s is greater than or equal to 2;
t is independently in each occurrence an integer of between about 0 and 4 inclusive; and
x is a real number between about 0 and 5 inclusive;
(b) between about 0 and 99 mole percent of one or more cyanate containing compounds.

2. The polytriazine of claim 1 wherein the cyanate-containing compound corresponds to the formula

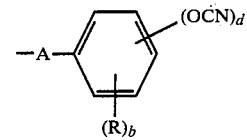

wherein
each R is the same or different or represents hydrogen, halogen, straight and branched C₁₋₂₀ alkyl, phenyl, alkoxy radicals having from 1 to 4 carbon atoms, alkoxy carbonyl radicals having from 1 to 4 carbon atoms in the alkyl group or; two adjacent radicals R on the same nucleus together form a carbocyclic 5- or 6-membered ring, two adjacent radicals R together with a hetero atom (O, S, N), form a 5- or 6-membered heterocyclic ring;

R' has the same meaning as R or represents the group

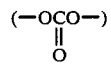

A represents a direct bond or a C₁₋₂₀ alkylene group unsubstituted or substituted by C₁₋₄ alkyl or phenyl, a cycloaliphatic or aromatic 5- or 6-membered ring, or a cycloaliphatic or aromtic 5- or 6-membered ring interrupted by oxygen, a sulfonyl group (—SO₂—), a carbonyl dioxide group, $$(-O\overset{\overset{\displaystyle O}{\|}}{C}O-)$$

or a carbonyl group;
a represents a number of from 1 to 5 when e≧1, and a number of from 2 to 5 when e is 0;
b represents 5−a when e≧1 and 6−(a+d) when e is 0;
c represents 5−d;
d represents a number of from 0 to 5, and e represents 0, 1, 2, or 3,
with a proviso that the sum of a and d is always a number from 2 to 5.

3. A polytriazine which comprises the reaction product of
(a) between about 1 and 100 mole percent of an aromatic polycyanate which corresponds to the formula

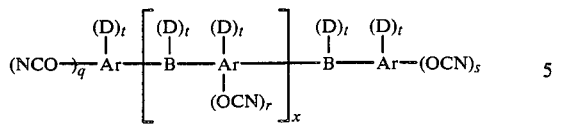

wherein

Ar is a benzene, naphthalene, phenanthracene, anthracene, or biaromatic radicals, or two or more aromatic radicals bridged by alkylene moieties;

B is

 II

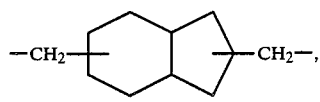 III

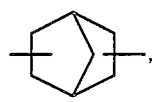 IV

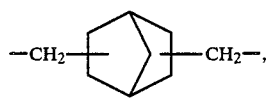 V

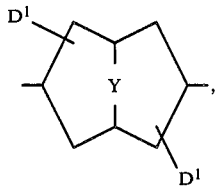 VI

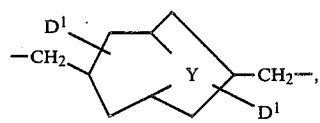 VII

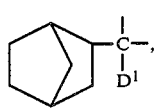 VIII

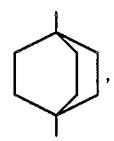 IX

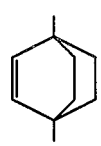 X

-continued

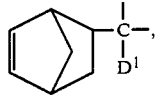 XI

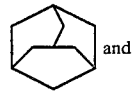 and XII

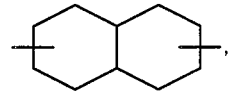 , XIII

D is an alkyl, alkenyl, alkynyl, aryl, alkaryl, aralkyl, halo, alkoxy, nitro, carboxylate, sulfone, sulfide, or carbonate moiety;
$D^1$ is $C_{1-5}$ alkyl;
Y is $CH_2$, S,

q, r, and s are independently 1 or 2;
t is independently 0, 1, or 2; and
x is a number between about 0 and 2 inclusive;
t is independently in each occurrence an integer of between about 0 and 4 inclusive; and
x is a number between about 0 and 5 inclusive;

(b) between about 0 and 99 mole percent of one or more cyanate containing compounds, which correspond to the formula $Ar(OCN)_n$ wherein Ar is defined hereinbefore and n is an integer of between 1 and 5 inclusive.

4. The polytriazine of claim 3 wherein the cyanate-containing compound corresponds to the formula $AR-OCN)_n$ wherein Ar is an aromatic radical and n is an integer of between 1 and 5, inclusive.

5. The polytriazine of claim 3 wherein:
Ar is a benzene, biphenyl, binaphthyl or diphenylalkylene radical;
B is

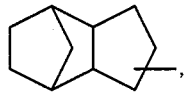 II

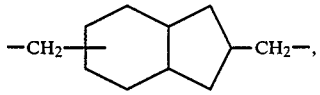 III

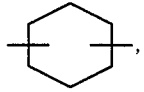 IV

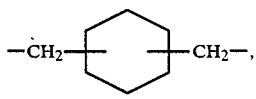 V

-continued

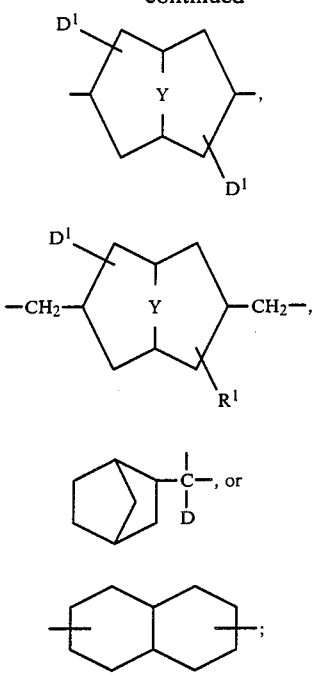

D is a $C_{1-10}$ alkyl, $C_{1-10}$ alkenyl, nitro or halo moiety;
q, r and s are 1;
t is 0 or 1; and
x is a number between 0 and 1 inclusive.

6. The polytriazine of claim 5 wherein:
Ar is benzene;
B is

 VI

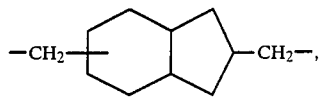 VII

 IV

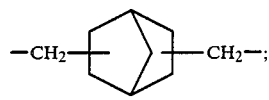 V

D is a $C_{1-3}$ alkyl, $C_{1-3}$ alkenyl, bromo or chloro moiety; and
t is 0.

7. The polytriazine of claim 6 wherein:
B is

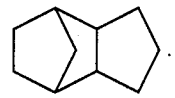

8. The polytriazine of claim 4 which comprises the reaction product of a polycyanate which corresponds to the formula

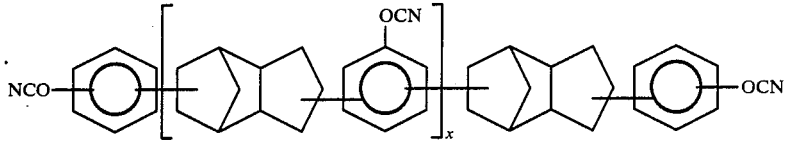

wherein x is a real number of between about 0 and 5, inclusive.

9. The polytriazine of claim 8 wherein x is a real number of between about 0 and 2, inclusive.

10. The polytriazine of claim 8 wherein x is a real number of between about 0 to 1, inclusive.

* * * * *

UNITED STATES PATENT AND TRADEMARK OFFICE
CERTIFICATE OF CORRECTION

PATENT NO. : 4,713,442

DATED : December 15, 1987

INVENTOR(S) : E.P. Woo et al.

Page 1 of 2

It is certified that error appears in the above-identified patent and that said Letters Patent is hereby corrected as shown below:

Cover page, under the heading "Related U.S. Application Data", line 1, delete "No. 522, 234" and insert -- No. 552,234 --;

Cover page, under the heading "Related U.S. Application Data", delete "1985" and insert -- 1983 --;

Cover page, under the heading "Other Publications", delete "87(8):54042e," and insert -- 86(26):140868K, --;

Col. 1, line 7, delete "Nov. 16, 1985", and insert -- Nov. 16, 1983 --;

Col. 7, line 53, delete "when $e \leq 1$", and insert -- when $e \geq 1$ --;

Col. 14, line 57 & 58, delete "when e is 0;" and insert --when $e = 0$ --;

Col. 16, line 42, delete "AR--OCN)$_n$", and insert -- AR$\leftarrow$OCN)$_n$ --;

UNITED STATES PATENT AND TRADEMARK OFFICE
CERTIFICATE OF CORRECTION

PATENT NO. : 4,713,442

DATED : December 15, 1987

INVENTOR(S) : E. P. Woo et al

It is certified that error appears in the above-identified patent and that said Letters Patent is hereby corrected as shown below:

Col. 17, change formula VII as follows:

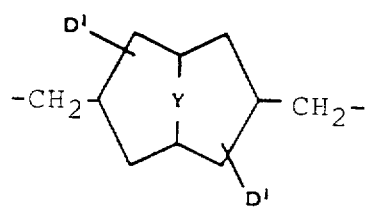

Signed and Sealed this

Twenty-first Day of July, 1992

*Attest:*

DOUGLAS B. COMER

*Attesting Officer*  *Acting Commissioner of Patents and Trademarks*